United States Patent
Chiba (10) Patent No.: US 10,722,155 B2
(45) Date of Patent: Jul. 28, 2020

(54) METHOD AND DEVICE FOR GENERATING IMAGE SHOWING CONCENTRATION DISTRIBUTION OF BIOLOGICAL SUBSTANCES IN BIOLOGICAL TISSUE

(71) Applicant: HOYA CORPORATION, Tokyo (JP)

(72) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 1012 days.

(21) Appl. No.: 14/894,119

(22) PCT Filed: May 28, 2014

(86) PCT No.: PCT/JP2014/064055
§ 371 (c)(1),
(2) Date: Nov. 25, 2015

(87) PCT Pub. No.: WO2014/192781
PCT Pub. Date: Dec. 4, 2014

(65) Prior Publication Data
US 2016/0120449 A1  May 5, 2016

(30) Foreign Application Priority Data

May 30, 2013 (JP) ................................ 2013-114703

(51) Int. Cl.
*A61B 5/00* (2006.01)
*A61B 5/1455* (2006.01)
(Continued)

(52) U.S. Cl.
CPC ...... *A61B 5/14551* (2013.01); *A61B 1/00009* (2013.01); *A61B 1/04* (2013.01);
(Continued)

(58) Field of Classification Search
CPC ............ A61B 5/14551; A61B 5/14546; A61B 5/1459; A61B 5/7225; A61B 1/00009;
(Continued)

(56) References Cited

U.S. PATENT DOCUMENTS 3,972,614 A * 8/1976 Johansen ................ G01N 1/286
356/36
4,324,556 A * 4/1982 Robertson ............ G01N 33/721
356/40

(Continued)

FOREIGN PATENT DOCUMENTS

CN    103070658    5/2013
CN    103654687    3/2014
(Continued)

OTHER PUBLICATIONS

US 9,560,957 B2, 02/2017, Yokouchi et al. (withdrawn)
(Continued)

*Primary Examiner* — Joanne M Hoffman
(74) *Attorney, Agent, or Firm* — Greenblum & Bernstein, P.L.C.

(57) ABSTRACT

Generating an image of a molar concentration ratio between a first and second biological substance, an absorption spectrum of the first and second biological substance within a predetermined wavelength range including a first, second, third, and fourth isosbestic point, acquiring first imaging data of the tissue using light extracted from white light using a first filter to collectively selectively extract light in a first wavelength range demarcated by the first and second isosbestic point, light in a second wavelength range demarcated by the second and third isosbestic point, and light in a third wavelength range demarcated by the third and fourth isosbestic point; acquiring second imaging data by taking an image of the tissue using light from the white light using a second optical filter to selectively extract light in the second
(Continued)

wavelength range; and generating the distribution image on the basis of the first and second imaging data.

3 Claims, 6 Drawing Sheets

(51) Int. Cl.
*A61B 5/1459* (2006.01)
*A61B 1/06* (2006.01)
*G06T 7/00* (2017.01)
*A61B 1/00* (2006.01)
*A61B 1/04* (2006.01)
*A61B 5/145* (2006.01)

(52) U.S. Cl.
CPC .......... *A61B 1/0638* (2013.01); *A61B 1/0646* (2013.01); *A61B 5/1459* (2013.01); *A61B 5/14546* (2013.01); *A61B 5/7225* (2013.01); *G06T 7/0012* (2013.01); *G06T 2207/10024* (2013.01); *G06T 2207/10068* (2013.01)

(58) Field of Classification Search
CPC ....... A61B 1/04; A61B 1/0638; A61B 1/0646; G06T 7/0012
See application file for complete search history.

(56) References Cited

U.S. PATENT DOCUMENTS

| | | | |
|---|---|---|---|
| 5,198,977 A * | 3/1993 | Salb | A61B 5/14553 356/40 |
| 5,408,998 A * | 4/1995 | Mersch | A61B 1/042 600/333 |
| 5,494,032 A * | 2/1996 | Robinson | A61B 5/14542 356/41 |
| 7,892,169 B2 | 2/2011 | Gono et al. | |
| 7,949,387 B2 | 5/2011 | Khoobehi et al. | |
| 8,681,208 B2 | 3/2014 | Yoshino | |
| 8,913,111 B2 | 12/2014 | Takahashi | |
| 9,277,190 B2 | 3/2016 | Igarashi et al. | |
| 9,370,297 B2 | 6/2016 | Yokouchi et al. | |
| 9,414,741 B2 | 8/2016 | Yamamoto | |
| 9,591,966 B2 | 3/2017 | Yokouchi et al. | |
| 2002/0086432 A1* | 7/2002 | Tam | G01N 21/3151 436/66 |
| 2002/0175993 A1 | 11/2002 | Ueno et al. | |
| 2003/0060684 A1 | 3/2003 | Ayame et al. | |
| 2003/0158470 A1 | 8/2003 | Wolters et al. | |
| 2003/0176768 A1 | 9/2003 | Gono et al. | |
| 2004/0075812 A1* | 4/2004 | Kardon | A61B 3/0058 351/206 |
| 2005/0027166 A1 | 2/2005 | Matsumoto et al. | |
| 2006/0018031 A1 | 1/2006 | Takasugi | |
| 2008/0312533 A1* | 12/2008 | Balberg | A61B 5/14546 600/437 |
| 2009/0069653 A1 | 3/2009 | Yoshida et al. | |
| 2009/0137908 A1 | 5/2009 | Patwardhan | |
| 2009/0225277 A1* | 9/2009 | Gil | A61B 5/14555 351/206 |
| 2010/0106013 A1 | 4/2010 | Morishita | |
| 2010/0140461 A1* | 6/2010 | Sprigle | G01J 3/2823 250/226 |
| 2010/0168584 A1 | 7/2010 | Fujinuma et al. | |
| 2010/0331624 A1 | 12/2010 | Suzuki et al. | |
| 2011/0230715 A1 | 9/2011 | Saito | |
| 2011/0237915 A1 | 9/2011 | Yamaguchi | |
| 2011/0254937 A1 | 10/2011 | Yoshino | |
| 2012/0116159 A1 | 5/2012 | Mizuyoshi et al. | |
| 2012/0116192 A1 | 5/2012 | Saito | |
| 2012/0157768 A1 | 6/2012 | Saito | |
| 2012/0215066 A1 | 8/2012 | Akiyama et al. | |
| 2012/0253158 A1* | 10/2012 | Yamaguchi | A61B 1/0638 600/339 |
| 2012/0302847 A1 | 11/2012 | Ozawa et al. | |
| 2012/0327205 A1 | 12/2012 | Takahashi | |
| 2013/0039147 A1 | 2/2013 | Witte et al. | |
| 2013/0158413 A1* | 6/2013 | Lisogurski | A61B 5/14551 600/476 |
| 2013/0162790 A1 | 6/2013 | Tanaka et al. | |
| 2013/0245419 A1 | 9/2013 | Oishi | |
| 2013/0289373 A1 | 10/2013 | Yamamoto | |
| 2013/0310668 A1 | 11/2013 | Young | |
| 2013/0345517 A1 | 12/2013 | Morimoto et al. | |
| 2014/0012113 A1* | 1/2014 | Kaku | A61B 1/06 600/339 |
| 2014/0066733 A1 | 3/2014 | Saito | |
| 2014/0152790 A1 | 6/2014 | Saito et al. | |
| 2014/0185907 A1 | 7/2014 | Chiba | |
| 2014/0235973 A1 | 8/2014 | Brittenham et al. | |
| 2015/0238126 A1* | 8/2015 | Saito | A61B 5/742 600/339 |
| 2015/0238127 A1* | 8/2015 | Saito | A61B 5/1459 600/339 |
| 2016/0058348 A1* | 3/2016 | Morimoto | A61B 5/14552 600/339 |
| 2016/0120449 A1 | 5/2016 | Chiba | |

FOREIGN PATENT DOCUMENTS

| | | |
|---|---|---|
| CN | 103654690 | 3/2014 |
| CN | 103796566 | 5/2014 |
| CN | 105324064 | 2/2016 |
| EP | 2449950 | 5/2012 |
| EP | 2468187 | 6/2012 |
| EP | 2689712 | 1/2014 |
| EP | 2702938 | 3/2014 |
| EP | 3005933 | 4/2016 |
| JP | 6-79594 | 10/1994 |
| JP | 2001-314370 | 11/2001 |
| JP | 2002-95635 | 4/2002 |
| JP | 2002-175702 | 6/2002 |
| JP | 2003-93343 | 4/2003 |
| JP | 3559755 | 9/2004 |
| JP | 3583731 | 11/2004 |
| JP | 3607857 | 1/2005 |
| JP | 2006-39043 | 2/2006 |
| JP | 2007-29453 | 2/2007 |
| JP | 2011-10998 | 1/2011 |
| JP | 2011-224038 | 11/2011 |
| JP | 2012-100800 | 5/2012 |
| JP | 2012-143348 | 8/2012 |
| JP | 2012-235962 | 12/2012 |
| JP | 2012-245223 | 12/2012 |
| JP | 2013-39215 | 2/2013 |
| JP | 2013-63097 | 4/2013 |
| JP | 5362149 | 12/2013 |
| JP | 2014-230647 | 12/2014 |
| JP | 2014-233344 | 12/2014 |
| WO | 2008/093745 | 8/2008 |
| WO | 2010/044432 | 4/2010 |
| WO | 2011/080996 | 7/2011 |
| WO | 2011/099322 | 8/2011 |
| WO | 2011/162111 | 12/2011 |
| WO | 2012/047806 | 4/2012 |
| WO | 2012/090552 | 7/2012 |
| WO | 2013/047054 | 4/2013 |
| WO | 2014/192781 | 12/2014 |

OTHER PUBLICATIONS

ThermoFisher Scientific, "Overview of Filters and Light Sources".*
Pierce, M., "Optical Contrast agents and imaging systems for detection and diagnosis of cancer", Int J Cancer, 2010.*
Furukawa,"In vivo absorption spectroscopy for absolute measurement", OSA, 3(10), 2012 (Year: 2012).*
Robles, "Assessing hemoglobin concentration using spectroscopic optical coherence tomography for feasibility of tissue diagnostics", OSA, 1(1), 2010 (Year: 2010).*
U.S. Appl. No. 15/295,048 to Fumika Yokouchi et al., filed Oct. 17, 2016.

(56) References Cited

OTHER PUBLICATIONS

International Search Reporting (ISR) in International Application PCT/JP2016/058112, dated Jun. 7, 2016.
Office Action in U.S. Appl. No. 15/295,048, dated Nov. 22, 2016.
U.S. Appl. No. 15/308,479 to Fumika Yokouchi, filed Nov. 2, 2016.
Office Action issued in European Patent Appl. No. 15183306.8, dated Jan. 24, 2017.
Office Action issued in U.S. Appl. No. 14/837,300, dated Apr. 13, 2018.
European Search Report issued in European Patent Application No. 15195635.6, dated Apr. 18, 2016.
European Search Report issued in European Patent Application No. 15183306.8, dated Feb. 5, 2016.
Extended European Search Report issued in European Patent Appl. No. 14805121.2, dated Mar. 20, 2017.
U.S. Appl. No. 14/936,965 to Toru Chiba, filed Nov. 10, 2015.
U.S. Appl. No. 14/837,300 to Toru Chiba, filed Aug. 27, 2015.
Office Action issued in related U.S. Appl. No. 14/837,300, dated Oct. 10, 2018.
Office Action issued in related U.S. Appl. No. 14/936,965, dated Dec. 15, 2017.
Office Action issued in China Patent Appl. No. 201510549104.2, dated Apr. 18, 2017, along with an english translation thereof.
Office Action issued in Japan Patent Appl. No. 2014-179036, dated Feb. 23, 2017.
Office Action issued in U.S. Appl. No. 15/295,048, dated Apr. 12, 2017.
Extended European Search Report issued in European Patent Appl. No. 16175262.1, dated Nov. 17, 2016.
Office Action issued in Japan Patent Appl. No. 2012-180902, dated May 24, 2016, along with an English translation thereof.
Office Action issued in China Patent Appl. No. 201310358808.2, dated Jun. 24, 2016, along with an English translation thereof.
Office Action issued in China Patent Appl. No. 201310358808.2, dated Nov. 4, 2015, along with an English translation thereof.
Office Action issued in Japan Patent Appl. No. 2012-180902, dated Dec. 26, 2016, along with an English translation thereof.
Office Action issued in China Patent Appl. No. 201310358808.2, dated Jan. 16, 2017, along with an English translation thereof.

* cited by examiner

METHOD AND DEVICE FOR GENERATING IMAGE SHOWING CONCENTRATION DISTRIBUTION OF BIOLOGICAL SUBSTANCES IN BIOLOGICAL TISSUE

TECHNICAL FIELD

The present invention relates to a method and a device for generating an image showing concentration distribution of biological substances in a biological tissue.

BACKGROUND ART

Recently, an endoscope device having a function of photographing spectroscopic image (spectral endoscope device) has been proposed. By using such a spectral endoscope device, it is possible to obtain information concerning spectral property (e.g., reflection spectrum) of a biological tissue such as a mucous membrane of a digestive organ. It is known that the reflection spectrum of a biological tissue reflects information concerning types or densities of components contained in the vicinity of a surface layer of a biological tissue being a measurement target. Specifically, it is known that an absorbance calculated from the reflection spectrum of a biological tissue equals to an absorbance obtained by linearly superimposing absorbances of a plurality of substances that compose the biological tissue.

It is known that composition and amount of substances in a lesion biological tissue differ from those in a healthy biological tissue. It is reported in many of the earlier studies that abnormalities of lesions represented by such as cancer are particularly deeply related to a condition of blood, especially to an overall amount of blood or oxygen saturation. Qualifying and quantifying two focused biological tissues by using spectroscopic feature values within the visible range that the two focused biological tissues have is a frequently used method in the field of spectrographic analysis. Therefore, it is possible to estimate existence of some kind of lesions in a biological tissue by comparing a spectral characteristic of blood in a biological tissue that includes lesions with a spectral characteristic of blood in a biological tissue that does not include lesions.

A spectral image is composed of a series of image information taken using light of different wavelengths, and more detailed spectral information of a biological tissue can be obtained from the spectral image having higher wavelength resolutions (i.e., larger number of wavelengths used to acquire image information). Patent Document 1 discloses an exemplary configuration of a spectral endoscope device which acquires spectral images in a wavelength range of 400-800 nm at 5 nm intervals.

PRIOR ART DOCUMENT

Patent Document (Patent Document 1) Japanese Patent Provisional Publication No. 2012-245223A

SUMMARY OF THE INVENTION

Problem to be Solved

However, in order to acquire spectral images having high wavelength resolutions, such as the spectral images disclosed in Patent Document 1, lots of images need to be taken while changing an image pick-up wavelength. Furthermore, a large amount of calculation is necessary to analyze lots of images and thus it takes time to analyze them. That is, relatively complicated photographing operations and calculations needs to be repeated to obtain effective diagnosis support information. Accordingly, there is a problem that it takes time to obtain the effective diagnosis support information.

The present invention is made in view of the above situation, and the object of the present invention is to provide a method and a device capable of acquiring image information showing distributions of biological substances, such as oxygen saturation distribution, in a short time.

Means for Solving the Problem

According to an embodiment of the present invention, there is provided a method for generating a distribution image showing a molar concentration ratio between a first biological substance and a second biological substance included in a biological tissue of which an absorption spectrum within a predetermined wavelength range has a first isosbestic point, a second isosbestic point, a third isosbestic point and a fourth isosbestic point in ascending order of wavelength, comprising: a step of acquiring first imaging data $G_1$ by taking an image of the biological tissue using light extracted from white light using a first optical filter configured to collectively selectively extract light in a first wavelength range demarcated by the first isosbestic point and the second isosbestic point, light in a second wavelength range demarcated by the second isosbestic point and the third isosbestic point, and light in a third wavelength range demarcated by the third isosbestic point and the fourth isosbestic point; a step of acquiring second imaging data $G_2$ by taking an image of the biological tissue using light extracted from the white light using a second optical filter configured to selectively extract light in the second wavelength range; and a step of generating the distribution image on the basis of the first imaging data $G_1$ and the second imaging data $G_2$.

Also, in the above method, the step of generating the distribution image on the basis of the first imaging data $G_1$ and the second imaging data $G_2$ may further comprise: a step of acquiring an absorbance $A_1$ of the biological tissue in a transmission wavelength range of the first optical filter on the basis of the first imaging data $G_1$; a step of acquiring an absorbance $A_2$ of the biological tissue in a transmission wavelength range of the second optical filter on the basis of the second imaging data $G_2$; and a step of generating the distribution image on the basis of the absorbance $A_1$ and the absorbance $A_2$.

Also, in the above method, the step of acquiring the absorbance $A_1$ may include a step of calculating the absorbance $A_1$ using Expression 1 or Expression 2; and $$A_1 = -\log G_1 \quad \text{(EXPRESSION 1)}$$

$$A_1 = -G_1 \quad \text{(EXPRESSION 2)}$$

the step of acquiring the absorbance $A_2$ may include a step for calculating the absorbance $A_2$ using Expression 3 or Expression 4.

$$A_2 = -\log G_2 \quad \text{(EXPRESSION 3)}$$

$$A_2 = -G_2 \quad \text{(EXPRESSION 4)}$$

Also, in the above method, the step of generating the distribution image on the basis of the absorbance $A_1$ and the absorbance $A_2$ may include: a step of calculating an index X using Expression 5; and $$X = A_1 - 2kA_2 \quad \text{(EXPRESSION 5)}$$

(where k is a constant)
a step for generating the distribution image on the basis of the index X.

Also, in the above method, the constant k may be 1.

Also, the above method may further comprise a step of acquiring third imaging data $R_3$ by taking an image of the biological tissue using light extracted from the white light using a third optical filter configured to selectively extract light in a fourth wavelength range in which an absorbance of the biological tissue is sufficiently low compared to an absorbance in the predetermined wavelength range, and the step of acquiring the absorbance $A_1$ may include: a step of calculating a first standardized reflectivity $SR_1$ by dividing the first imaging data $G_1$ by the third imaging data $R_3$; and a step of calculating the absorbance $A_1$ using Expression 6 or Expression 7, and $$A_1 = -\log SR \quad \text{(EXPRESSION 6)}$$

$$A_1 = -SR \quad \text{(EXPRESSION 7)}$$

the step of acquiring the absorbance $A_2$ may include: a step of calculating a second standardized reflectivity $SR_2$ by dividing the second imaging data $G_2$ by the third imaging data $R_3$; and a step of calculating the absorbance $A_2$ using Expression 8 or Expression 9.

$$A_2 = -\log SR_2 \quad \text{(EXPRESSION 8)}$$

$$A_2 = -SR_2 \quad \text{(EXPRESSION 9)}$$

Also, the above method may further comprise: a step of acquiring a first baseline image data $BL_1$ by taking an image of a colorless color reference board using light extracted from the white light using the first optical filter; and a step of acquiring a second baseline image data $BL_2$ by taking an image of the reference board using light extracted from the white light using the second optical filter, and the step of calculating the first standardized reflectivity $SR_1$ may include a step of dividing the first imaging data $G_1$ by the first baseline image data $BL_1$, and the step of calculating the second standardized reflectivity $SR_2$ may include a step of dividing the second imaging data $G_2$ by the second baseline image data $BL_2$.

Also, in the above method, the fourth wavelength range may be 650 nm band, and the third imaging data $R_3$ may be imaging data taken by a light-receiving element, to which an R filter is provided, included in an image pick-up device provided with an RGB color filter.

Also, in the above method, the constant k may be determined such that the index X, acquired on the basis of the first imaging data $G_1$ and the second imaging data $G_2$ acquired by taking images of a biological tissue of which the molar concentration ratio is known, becomes closest to a theoretical index X.

Also, in the above method, the measured index X for each of a plurality of biological tissues, each having a known molar concentration ratio that is different from each other, may be acquired and the constant k may be determined such that a calibration curve showing a relationship between the known molar concentration ratio and the measured index X becomes closest to a reference line showing a relationship between the known molar concentration ratio and the theoretical index X.

Also, in the above method, the light extracted from the white light using the first optical filter in the step of acquiring the first imaging data $G_1$ may be dimmed such that an exposure when acquiring the first imaging data $G_1$ and an exposure when acquiring the second imaging data $G_2$ become equivalent.

Also, in the above method, the two types of biological substances may be oxyhemoglobin and deoxyhemoglobin, and the molar concentration ratio of the first biological substance and the second biological substance included in the biological tissue may be oxygen saturation.

Also, in the above method, the predetermined wavelength range may be a Q band of hemoglobin, and the first imaging data $G_1$ and the second imaging data $G_2$ may be imaging data taken by a light-receiving element, to which a G filter is provided, included in an image pick-up device provided with an RGB color filter.

Further, according to an embodiment of the present invention, there is provided a device for generating a distribution image showing a molar concentration ratio between a first biological substance and a second biological substance included in a biological tissue of which an absorption spectrum within a predetermined wavelength range has a first isosbestic point, a second isosbestic point, a third isosbestic point and a fourth isosbestic point in ascending order of wavelength, comprising: a light source which emits white light; a first optical filter configured to collectively selectively extract light in a first wavelength range demarcated by the first isosbestic point and the second isosbestic point, light in a second wavelength range demarcated by the second isosbestic point and the third isosbestic point, and light in a third wavelength range demarcated by the third isosbestic point and the fourth isosbestic point from the white light; a second optical filter configured to selectively extract light in the second wavelength range from the white light; a switching means configured to switch between the first optical filter and the second optical filter; an image pick-up device configured to take an image of the biological tissue using the light emitted by the light source; and an image processor unit configured to generate the distribution image on the basis of imaging data generated by the image pick-up device.

Also, the above device may be an endoscope device comprising an endoscope provided at a tip portion.

Effects of the Invention

According to the present invention, image information showing distributions of biological substances, such as oxygen saturation distribution, can be acquired in a short time.

EMBODIMENTS FOR CARRYING OUT THE INVENTION

In the following, an embodiment according to the present invention is described with reference to the accompanying drawings.

An endoscope device according to the embodiment of the present invention described below is a device that quantitatively analyzes biological information (e.g., oxygen saturation) of an object on the basis of a plurality of images taken using light of different wavelengths and displays the analysis result as images. In a quantitative analysis of the oxygen saturation described below, a characteristic that a spectral property of blood (i.e., spectral property of hemoglobin) continuously changes in accordance with the oxygen saturation is used.

(Principles for Calculation of Spectral Property of Hemoglobin and Oxygen Saturation)

Before explaining a detailed configuration of an endoscope device according to the embodiment of the present invention, principles for calculation of the spectral property of hemoglobin and the oxygen saturation used in the embodiment will be described.

Figure 1:
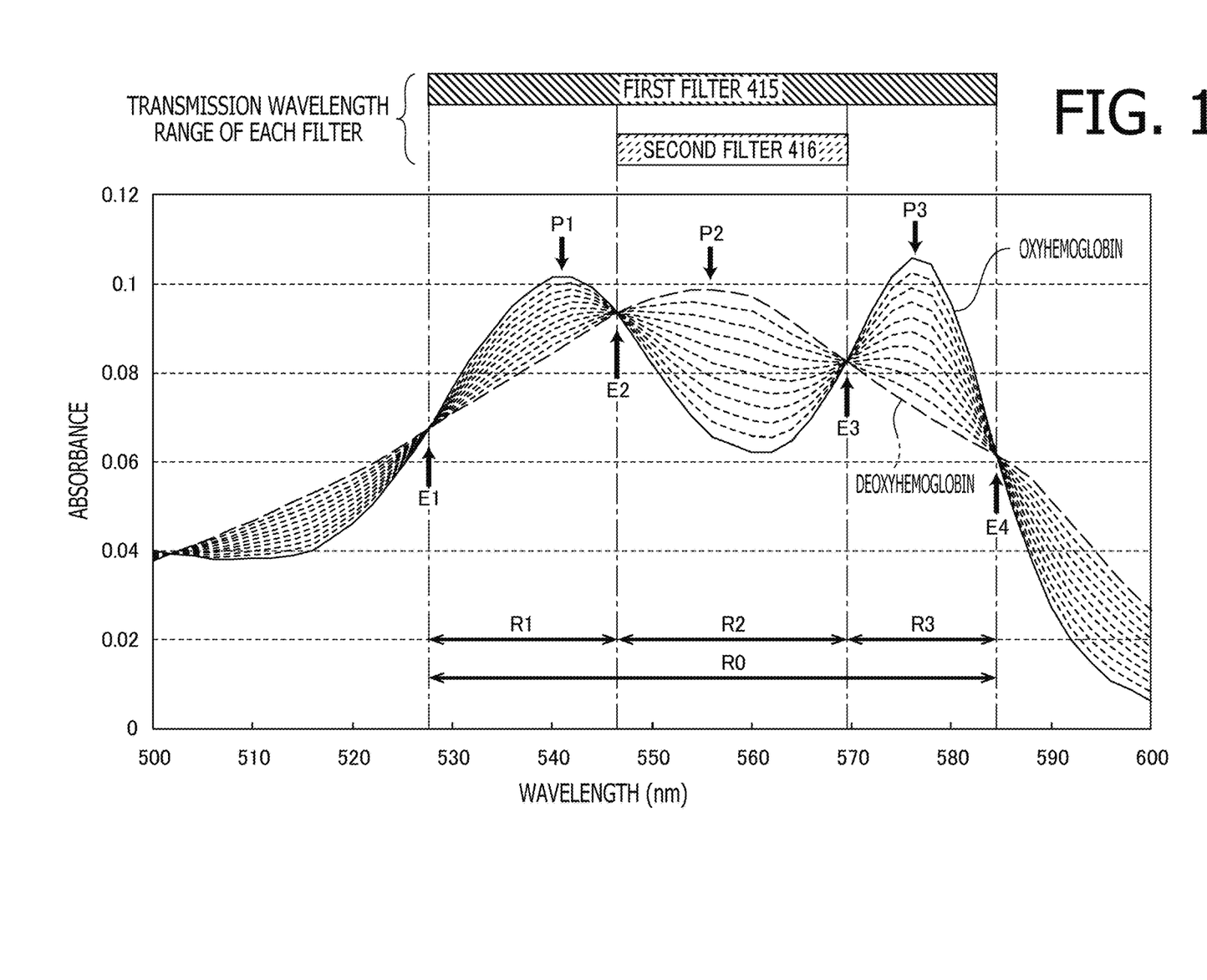
FIG. 1 shows an absorption spectrum of hemoglobin at Q band.

FIG. 1 shows an absorption spectrum of hemoglobin at wavelengths of around 550 nm. Hemoglobin has a strong absorption band, derived from porphyrin, called Q band at wavelengths of around 550 nm. The absorption spectrum of hemoglobin changes in accordance with the oxygen saturation (ratio of oxyhemoglobin to the overall hemoglobin). A waveform shown in a solid line in FIG. 1 is an absorption spectrum of hemoglobin when the oxygen saturation is 100% (i.e., an absorption spectrum of oxyhemoglobin HbO), and a waveform shown in a long-dashed line is an absorption spectrum of hemoglobin when the oxygen saturation is 0% (i.e., an absorption spectrum of deoxyhemoglobin Hb). Waveforms shown in short-dashed lines are absorption spectra of hemoglobin (a mixture of oxyhemoglobin and deoxyhemoglobin) at oxygen saturations of between 0% and 100% (10, 20, 30, . . . , 90%).

As shown in FIG. 1, at Q band, oxyhemoglobin and deoxyhemoglobin show peak wavelengths that differ from each other. Specifically, oxyhemoglobin has an absorption peak P1 at a wavelength of around 542 nm, and an absorption peak P3 at a wavelength of around 576 nm. On the other hand, deoxyhemoglobin has an absorption peak P2 at a wavelength of around 556 nm. Since FIG. 1 shows a two-component absorption spectrum in which a sum of a concentration of each component (oxyhemoglobin and deoxyhemoglobin) is constant, isosbestic points E1, E2, E3 and E4, where absorbances are constant regardless of the concentration of each component (i.e., oxygen saturation), appear. In the following description, a wavelength range between isosbestic points E1 and E2 is referred to as wavelength range R1, a wavelength range between isosbestic points E2 and E3 is referred to as wavelength range R2, and a wavelength range between isosbestic points E3 and E4 is referred to as wavelength range R3. Further, a wavelength range between isosbestic points E1 and E4 is referred to as wavelength range R0 (i.e., a combination of wavelengths ranges of R1, R2 and R3).

As shown in FIG. 1, between neighboring isosbestic points, absorbance of hemoglobin monotonically increases or decreases with the oxygen saturation. Further, between neighboring isosbestic points, absorbance of hemoglobin almost linearly changes with the oxygen saturation.

Specifically, absorbances $A_{R1}$ and $A_{R3}$ of hemoglobin at wavelength ranges R1 and R3 linearly increases with oxyhemoglobin concentration (oxygen saturation), and absorbance $A_{R2}$ of hemoglobin at wavelength range R2 linearly increases with deoxyhemoglobin concentration (1—"oxygen saturation"). Therefore, an index X, defined by the following Expression 10, linearly increases with oxyhemoglobin concentration (oxygen saturation).

$$X=(A_{R1}+A_{R3})-A_{R2} \qquad \text{(EXPRESSION 10)}$$

Therefore, the oxygen saturation can be calculated from the index X by experimentally acquiring a quantitative relationship between the oxygen saturation and the index X.

(Configuration of Endoscope Device)

Figure 2:
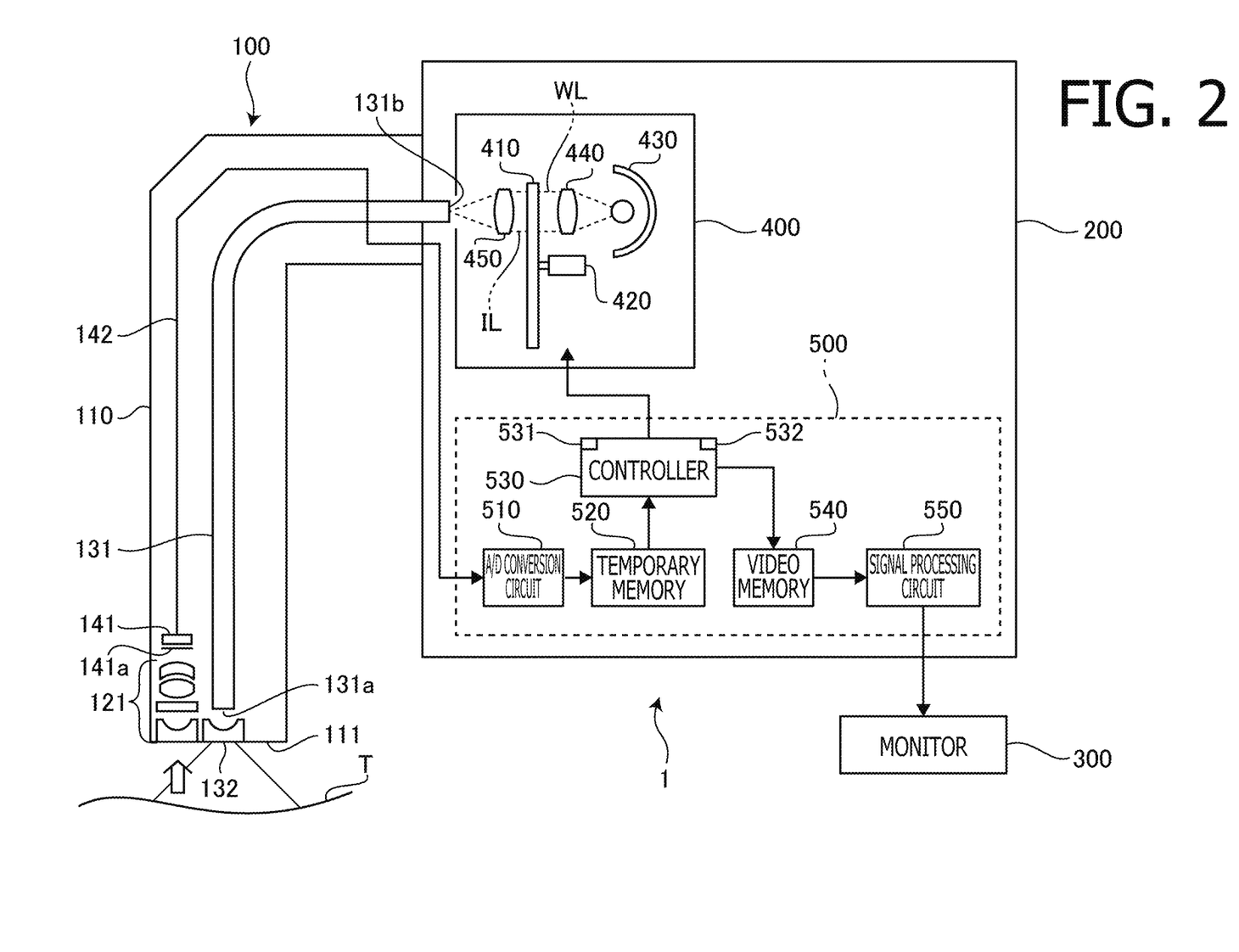
FIG. 2 is a block chart illustrating an endoscope device according to the embodiment of the present invention.

FIG. 2 is a block chart illustrating an endoscope device 1 according to the embodiment of the present invention. The endoscope device 1 of the present embodiment comprises an electronic endoscope 100, a processor 200 and a monitor 300. The electronic endoscope 100 and the monitor 300 are detachably connected to the processor 200. Also, the processor 200 includes therein a light source unit 400 and an image processor unit 500.

The electronic endoscope 100 has an insertion tube 110 to be inserted into a body cavity. The electronic endoscope 100 is provided with a light guide 131 which extends over the full length of the electronic endoscope 100. One end portion of the light guide 131 (a tip portion 131a) is arranged close to a tip portion of the insertion tube 110 (an insertion tube tip portion 111), and the other end portion of the light guide 131 (a proximal end portion 131b) is connected to the processor 200. The processor 200 includes therein the light source unit 400 comprising a light source lamp 430, e.g., a Xenon lamp which generates a large amount of white light WL. The illumination light IL generated by the light source unit 400 is incident on the end portion 131b of the light guide 131. The light which is incident on the proximal end portion 131b of the light guide 131 is guided to the tip portion 131a through the light guide 131, and is emitted from the tip portion 131a. At the insertion tube tip portion 111 of the electronic endoscope 100, a light distribution lens 132 is arranged to face the tip portion 131a of the light guide 131. The illumination light IL emitted from the tip portion 131a of the light guide 131 passes through the light distribution lens 132, and illuminates the biological tissue T near the insertion tube tip portion 111.

An objective optical system 121 and an image pick-up device 141 is provided at the insertion tube tip portion 111. A portion of light which is reflected or scattered by the surface of the biological tissue T (return light) is incident on the objective optical system 121 and condensed, and forms an image on a light-receiving surface of the image pick-up device 141. The image pick-up device 141 of the present embodiment is a color image photographing CCD (Charge Coupled Device) image sensor comprising a color filter 141a on a light-receiving surface thereof, but other types of image pick-up device such as CMOS (Complementary Metal Oxide Semiconductor) image sensor may also be used. The color filter 141a is a so-called on-chip filter, in which an R filter that transmits red light, a G filter that transmits green light, and a B filter that transmits blue light are arranged, which is directly formed on each light-receiving element of the image pick-up device 141. Each of the R filter, G filter and B filter has a spectral property shown in FIG. 3. That is, the R filter of the present embodiment is a filter that transmits light having wavelengths of longer than about 570 nm, the G filter is a filter that transmits light having wavelengths of between about 470-620 nm, and the B filter is a filter that transmits light having wavelengths of shorter than about 530 nm.

The image pick-up device 141 is controlled to drive in synchronization with a signal processing circuit 550 which will be described later, and periodically (e.g., at ⅓₀ seconds interval) outputs imaging signals corresponding to an image formed on the light-receiving surface. The imaging signals which are outputted from the image pick-up device 141 are sent to the image processor unit 500 of the processor 200 via a cable 142.

The image processor unit 500 comprises an A/D conversion circuit 510, a temporary memory 520, a controller 530, a video memory 540 and a signal processing circuit 550. The A/D conversion circuit 510 executes A/D conversion to the image signals transmitted from the image pick-up device 141 of the electronic endoscope 100 via the cable 142 to output digital image data. The digital image data outputted from the A/D conversion circuit 510 is transmitted to and stored in the temporary memory 520. The digital image data (imaging signals) includes R digital image data (R imaging signal) which is imaged by the light-receiving element to which the R filter is provided, G digital image data (G imaging signal) which is taken by the light-receiving element to which the G filter is provided, and B digital image data (B imaging signal) which is taken by the light-receiving element to which the B filter is provided.

The controller 530 processes a piece of or a plurality of pieces of image data stored in the temporary memory 520 to generate one piece of display image data, and transmits the display image data to the video memory 540. For example, the controller 530 generates display image data such as display image data generated from a piece of digital image data, display image data in which a plurality of pieces of image data are arranged, or display image data in which healthy regions and lesion regions are identified or a graph of a reflection spectrum of the biological tissue T corresponding to a specific pixel (x, y) is displayed by generating a reflection spectrum of the biological tissue T for each pixel (x, y) on the basis of a plurality of pieces of digital image data, and stores them in the video memory 540. The signal processing circuit 550 generates video signals having a predetermined format (e.g., a format which conforms to NTSC or DVI standard) on the basis of the display image data stored in the video memory 540, and outputs the video signals. The video signals outputted from the signal processing circuit 550 is inputted to the monitor 300. As a result, endoscopic images taken by the electronic endoscope 100 and the like are displayed on the monitor 300.

As described above, the processor 200 has both a function as a video processor for processing the image signals outputted from the image pick-up device 141 of the electronic endoscope 100, and a function as a light source device for supplying illumination light IL to the light guide 131 of the electronic endoscope 100 to illuminate the biological tissue T being an object.

Other than the above-mentioned light source 430, the light source unit 400 comprises a collimator lens 440, a rotating filter 410, a filter control unit 420 and a condenser lens 450. The white light WL emitted from the light source 430 is converted by the collimator lens 440 into a collimated beam, transmits through the rotating filter 410, and then is incident on the end portion 131b of the light guide 131 by the condenser lens 450.

The rotating filter 410 is a circular plate type optical unit comprising a plurality of optical filters, and is configured such that a transmission wavelength range thereof changes in accordance with the rotation angle thereof. The rotation angle of the rotating filter 410 is controlled by the filter control unit 420 connected to the controller 530. The spectrum of the illumination light supplied to the light guide 131 through the rotating filter 410 can be switched by the controller 530 controlling the rotation angle of the rotating filter 410 via the filter control unit 420.

Figure 4:
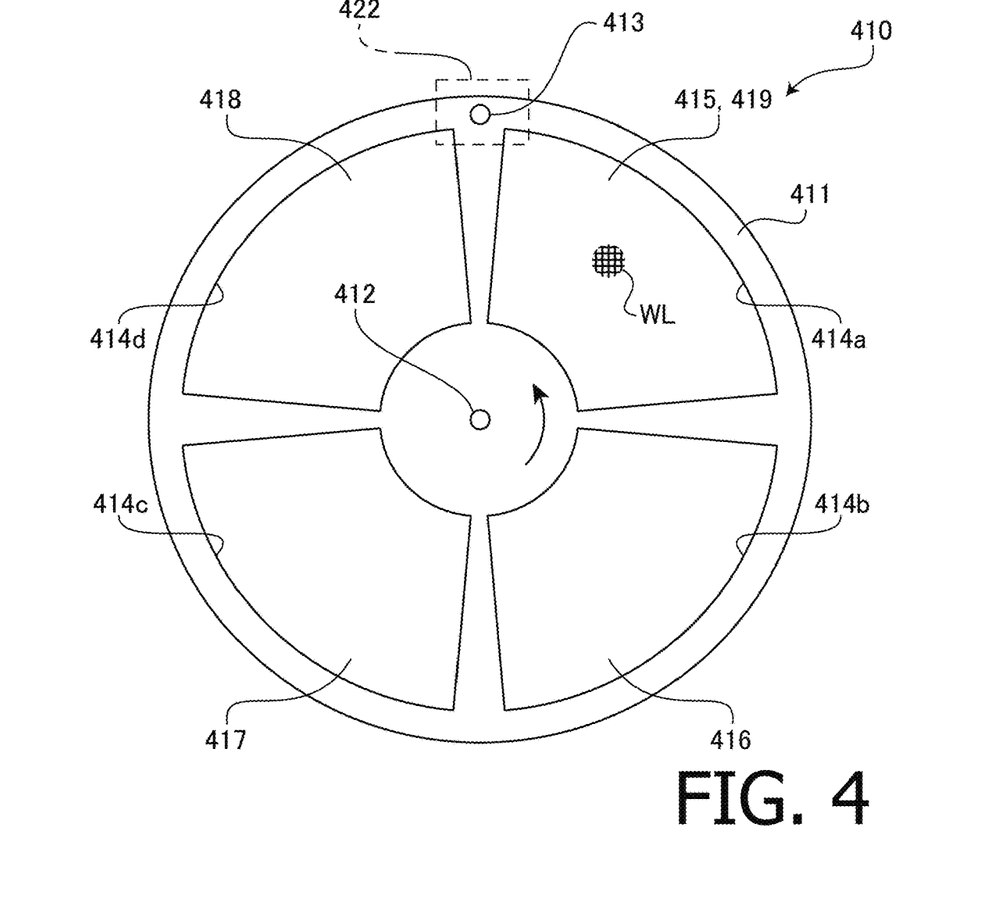
FIG. 4 is an external view of a rotating filter.

FIG. 4 is an external view (front view) of the rotating filter 410. The rotating filter 410 comprises a substantially circular plate shaped frame 411, and four fan-shaped optical filters 415, 416, 417, and 418. Around the central axis of the frame 411, four fan-shaped windows 414a, 414b, 414c, and 414d are formed at regular intervals, and the optical filters 415, 416, 417, and 418 are fit into each of the windows 414a, 414b, 414c, and 414d, respectively. It is noted that, although the optical filters of the present embodiment are all dielectric multilayer film filters, other types of optical filters (e.g., absorbing type optical filters or etalon filters in which dielectric multilayers are used as reflecting layers) may also be used.

Also, a boss hole 412 is formed on the central axis of the frame 411. An output axis of a servo motor (not shown) included in the filter control unit 420 is inserted and fixed to the boss hole 412, and the rotating filter 410 rotates along with the output axis of the servo motor.

FIG. 4 shows a state in which the white light WL is incident on the optical filter 415. However, as the rotating filter 410 rotates in a direction indicated by an arrow, the optical filter on which the white light WL is incident changes to 415, 416, 417, 418 in this order, and thus the spectrum of the illumination light IL that transmits the rotating filter 410 can be switched.

The optical filters 415 and 416 are optical band-pass filters that selectively transmit light of 550 nm band. As shown in FIG. 1, the optical filter 415 is configured to transmit light which is inside the wavelength range between isosbestic points E1 and E4 (i.e., wavelength range R0) with low loss, and to cut off light which is outside the wavelength range. Also, the optical filter 416 is configured to transmit light which is inside the wavelength range between isosbestic points E2 and E3 (i.e., wavelength range R2) with low loss, and to cut off light which is outside the wavelength range.

Figure 3:
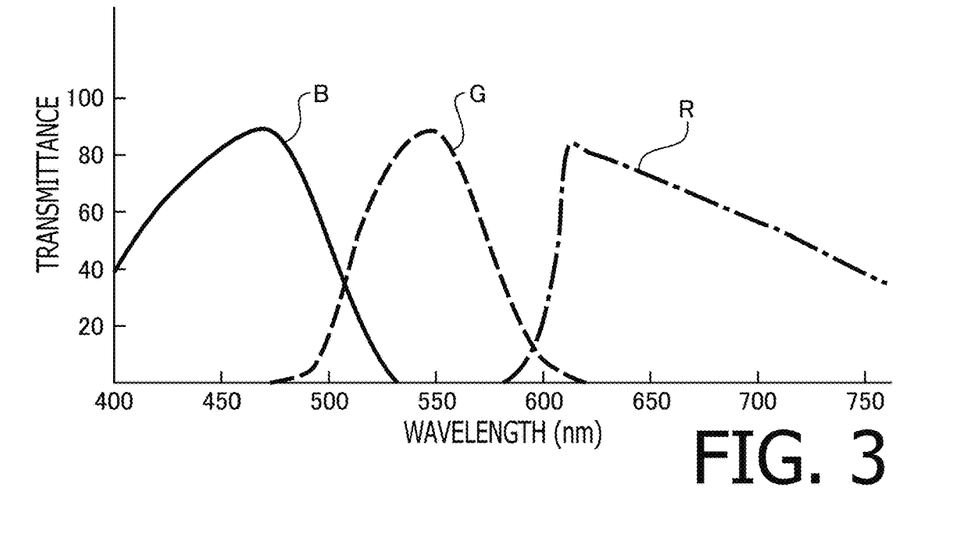
FIG. 3 shows transmission spectra of color filters which are accommodated in an image pick-up device.

The transmission wavelength ranges of the optical filters 415 and 416 (FIG. 1) are included in a transmission wavelength range of the G filter of the color filter 141a (FIG. 3). Therefore, an image which is formed by light that transmitted through the optical filter 415 or 416 is taken by the light-receiving element to which the G filter is provided, and is acquired as the G digital image data (G imaging signal).

The optical filter 417 is designed to selectively transmit only light of 650 nm band (630-650 nm) being a wavelength range in which an absorbance of hemoglobin in the biological tissue T is low. The transmission wavelength range of the optical filter 417 is included in a transmission wavelength range of the R filter of the color filter 141a (FIG. 3). Therefore, an image which is formed by light that transmitted through the optical filter 417 is taken by the light-receiving element to which the R filter is provided, and is acquired as the R digital image data (R imaging signal). The image data acquired by using the illumination light of 650 nm band is used in a standardization process which will be explained later.

Also, the optical filter 418 is an ultraviolet cut filter, and the illumination light IL (i.e., a white light) that transmitted through the optical filter 418 is used for taking normal observation images. It is noted that the rotating filter 410 may be configured without the optical filter 418 to leave the window 414d of the frame 411 open.

To the window 414a, a dimmer filter 419 is provided over the optical filter 415. The dimmer filter 419 does not have wavelength dependency throughout the visible light range and thus only decreases a light amount of the illumination light IL without changing the spectrum thereof. The light amount of the illumination light IL that transmitted through the optical filter 415 and the dimmer filter 419 are adjusted to a light amount substantially equivalent to a light amount of the illumination light IL that transmitted through the optical filter 416 by using the dimmer filter 419. Thus, images can be taken with a proper exposure with the same exposure time in both a case where the illumination light IL that passed through the optical filter 415 is used and a case where the illumination light IL that passed through the optical filter 416 is used.

In the present embodiment, a metal mesh having a fine mesh size is used as the dimmer filter 419. Apart from the metal mesh, other types of dimmer filter such as a half mirror type may be used. Further, transmittances of the optical filters 415 and 416 themselves may be adjusted instead of using the dimmer filter. Further, dimmer filters may also be provided to the windows 414c and 414d. Further, central angles of the windows 414a, 414b, 414c, and 414d (i.e., aperture areas) may be changed to adjust transmitting light amounts. Further, the exposure time may be changed for each optical filter instead of using the dimmer filter.

At the periphery of the frame 411, a through hole 413 is formed. The through hole 413 is formed at a position that is same as a position of boundary between the windows 414a and 414d in the rotating direction of the frame 411. Around the frame 411, a photo interrupter 422 for detecting the through hole 413 is arranged such that the photo interrupter 422 surrounds a portion of the periphery of the frame 411. The photo interrupter 422 is connected to the filter control unit 420.

The endoscope device 1 of the present embodiment has four operation modes of a normal observation mode, a spectral analysis (oxygen saturation distribution image displaying) mode, a baseline measuring mode and a calibration mode. The normal observation mode is an operation mode in which a color image is taken using a white light that transmitted through the optical filter 418. The spectral analysis mode is a mode in which a spectral analysis is carried out on the basis of the digital image data taken using illumination light that transmitted through the optical filters 415, 416 and 417, and a distribution image of biomolecules in a biological tissue (e.g., oxygen saturation distribution image) is displayed. The baseline measuring mode is a mode in which an image of a color reference board such as a colorless diffusion board (e.g., frosted glass) or reference reflection board is taken as an object using illumination light that passed through the optical filters 415, 416 and 417, before (or after) executing the actual endoscopic observation, to acquire data to be used in a standardization process which will be described later. The calibration mode is a process in which a spectral analysis is carried out for a sample of which properties such as the oxygen saturation is known, and a parameter (correction coefficient k which will be described later) is adjusted such that there is no difference between the analysis result and the theoretical value.

In the normal observation mode, the controller 530 controls the filter control unit 420 to immobilize the rotating filter 410 at a position where the white light WL is incident on the optical filter 418. Then, the digital image data taken by the image pick-up device 141 is converted to video signals after performing image processes as necessary, and is displayed on the monitor 300.

In the spectral analysis mode, the controller 530 controls the filter control unit 420 to drive the rotating filter 410 to rotate at constant rotation speed while sequentially taking images of the biological tissue T using illumination light that transmitted through the optical filters 415, 416, 417 and 418. Then, an image indicating distribution of biomolecules in the biological tissue is generated on the basis of digital image data acquired using each of the optical filters 415, 416 and 417. Then, a display image in which the distribution image and a normal observation image acquired by using the optical filter 418 are arranged is generated and converted to video signals, and is displayed on the monitor 300.

In the spectral analysis mode, the filter control unit 420 detects a rotational phase of the rotating filter 410 on the basis of timing the photo interrupter 422 detects the through hole 413, compares the rotational phase to a phase of a timing signal supplied by the controller 530, and adjusts the rotational phase of the rotating filter 410. The timing signal from the controller 530 is synchronized with a driving signal for the image pick-up device 141. Therefore, the rotating filter 410 is driven to rotate at a substantially constant rotation speed in synchronization with the driving of the image pick-up device 141. Specifically, the rotation of the rotating filter 410 is controlled such that the optical filter 415, 416, 417 or 418 (window 414a, b, c or d) on which the white light WL is to be incident switches each time one image (three frames: R, G and B) is taken by the image pick-up device 141.

In the baseline measuring mode, the controller 530 controls the filter control unit 420 to rotate the rotating filter 410 while sequentially taking images of the color reference board using the illumination light IL that transmitted through the optical filters 415, 416 and 417. Each piece of the G digital image data taken using the illumination light IL that transmitted through the optical filters 415 and 416 is stored in an internal memory 531 of the controller 530 as baseline image data $BL_{415}(x, y)$ and $BL_{416}(x, y)$, respectively. Further, the R digital image data taken using the illumination light IL that transmitted through the optical filter 417 is stored in the internal memory 531 of the controller 530 as baseline image data $BL_{417}(x, y)$.

Figure 5:
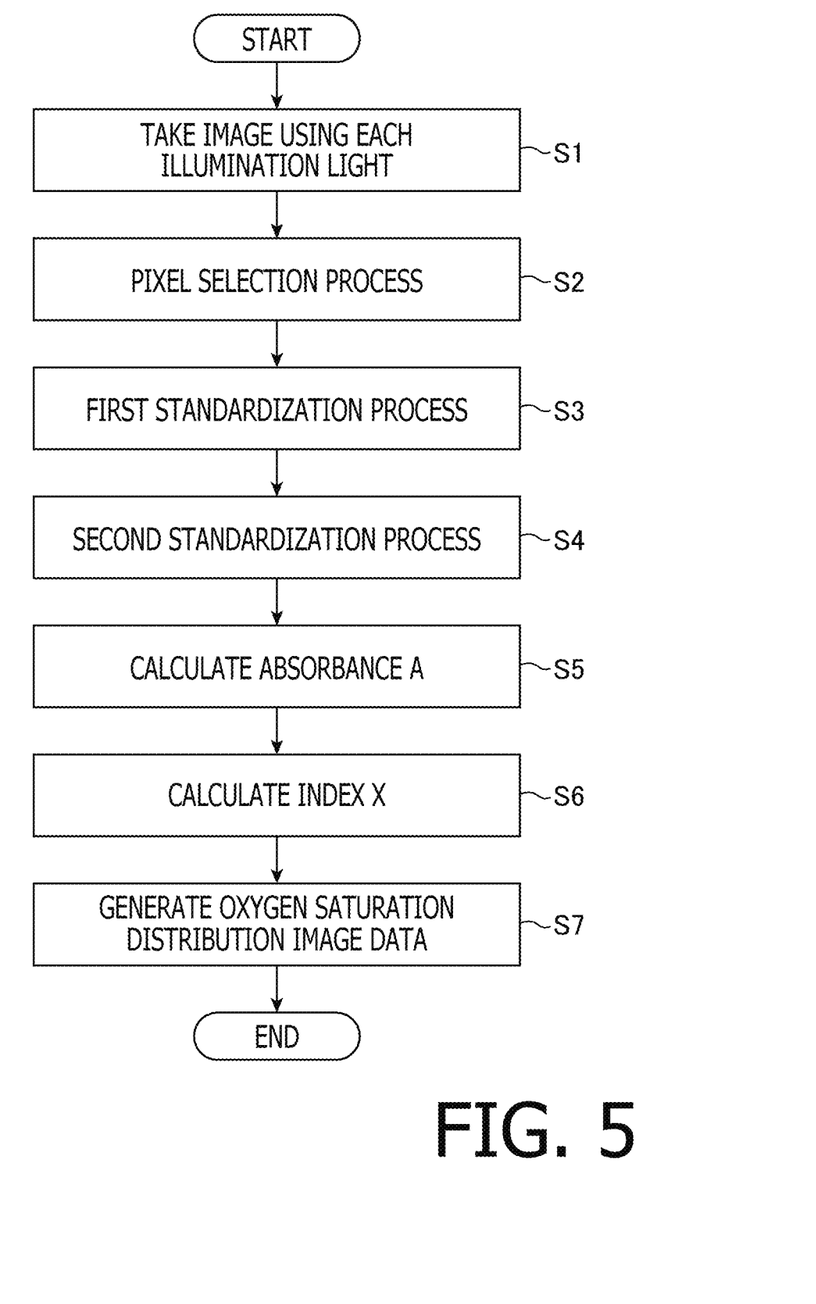
FIG. 5 is a flowchart explaining an image generating process according to the embodiment of the present invention.

Next, an image generation process executed by the image processor unit 500 in the spectral analysis mode will be described. FIG. 5 is a flow chart explaining the image generation process.

When the spectral analysis mode is selected by a user's operation, as described above, the filter control unit 420 drives the rotating filter 410 to rotate at constant rotation speed. Then, from the light source unit 400, the illumination light IL that transmitted through the optical filters 415, 416, 417 and 418 are sequentially supplied, and an image is sequentially taken using each of the illumination light IL (S1). Specifically, G digital image data $G_{415}(x, y)$ taken using the illumination light IL that transmitted through the optical filter 415, G digital image data $G_{416}(x, y)$ taken using the illumination light IL that transmitted through the optical filter 416, R digital image data $R_{417}(x, y)$ taken using the illumination light IL that transmitted through the optical filter 417, and R digital image data $R_{418}(x, y)$, G digital image data $G_{418}(x, y)$ and B digital image data $B_{418}(x, y)$ taken using the illumination light IL that transmitted through the optical filter (ultraviolet cut filter) 418 are stored in an internal memory 532 of the controller 530.

Then, the image processor unit 500 executes a pixel selection process S2 for selecting pixels to be targets of the following analyzing processes (processes S3-S7) by using the R digital image data $R_{418}$ (x, y), G digital image data $G_{418}$ (x, y) and B digital image data $B_{418}$ (x, y) acquired in the process S1. Even if the oxygen saturations or blood flow rates are calculated from color information of pixels corresponding to portions which do not contain blood or portions which colors of tissues are dominantly influenced by substances other than hemoglobin, meaningful values cannot be obtained and thus the values becomes mere noises. Calculating and providing such noises not only disturbs diagnosis by the doctor but also causes a bad effect by applying useless load to the image processor unit 500 to deteriorate processing speed. Therefore, the image generating process of the present embodiment is configured to select pixels that are appropriate to the analyzing process (i.e., pixels to which the spectral property of hemoglobin is recorded) and to execute the analyzing process to the selected pixels.

In the pixel selection process S2, only pixels which satisfy all the conditions expressed in Expression 11, Expression 12 and Expression 13 are selected as the targets of the analyzing process.

$$B_{418}(x,y)/G_{418}(x,y) > a_1 \quad \text{(EXPRESSION 11)}$$

$$R_{418}(x,y)/G_{418}(x,y) > a_2 \quad \text{(EXPRESSION 12)}$$

$$R_{418}(x,y)/B_{418}(x,y) > a_3 \quad \text{(EXPRESSION 13)}$$

where $a_1$, $a_2$ and $a_3$ are positive constants.

The above three conditional expressions are set on the basis of a value size relation, G component<B component<R component, in a transmission spectrum of blood. It is noted that the pixel selection process S2 may be executed using one or two of the above three conditional expressions (e.g., using Expression 12 and Expression 13 by focusing on a red color that is specific to blood).

Then, the image processor unit 500 executes the standardization process. The standardization process of the present embodiment includes a first standardization process S3 for correcting properties of the endoscope device 1 itself (e.g., transmittances of the optical filters and light receiving sensitivities of the image pick-up devices) and a second standardization process S4 for correcting reflectivity variations due to differences in surface states of the biological tissue T being an object and due to angles of incidence of the illumination light IL to the biological tissue T.

In the standardization process, the image processor unit 500 calculates a standardized reflectivity $SR_{415}$ (x, y) using the following Expression 14 by using the G digital image data $G_{415}$ (x, y) taken using the illumination light IL that transmitted through the optical filter 415, the R digital image data $R_{417}$ (x, y) taken using the illumination light IL that transmitted through the optical filter 417, and the baseline image data $BL_{415}$ (x, y) and $BL_{417}$ (x, y). It is noted that a component that is dependent on the properties of the endoscope device 1 (instrumental function) is removed by dividing each of the digital image data $G_{415}$ (x, y) and $R_{417}$ (x, y) by the respective baseline image data $BL_{415}$ (x, y) and $BL_{417}$ (first standardization process S3). Also, the reflectivity variations due to differences in surface states of the biological tissue T and angles of incidence of the illumination light to the biological tissue T is corrected by dividing the G digital image data $G_{415}$ (x, y) by the R digital image data $R_{417}$ (x, y) (second standardization process S4).

$$SR_{415}(x, y) = \frac{G_{415}(x, y)/BL_{415}(x, y)}{R_{417}(x, y)/BL_{417}(x, y)} \quad \text{(EXPRESSION 14)}$$

Similarly, a standardized reflectivity $SR_{416}$ (x, y) is calculated using the following Expression 15.

$$SR_{416}(x, y) = \frac{G_{416}(x, y)/BL_{416}(x, y)}{R_{417}(x, y)/BL_{417}(x, y)} \quad \text{(EXPRESSION 15)}$$

Absorbances $A_{415}$ (x, y) and $A_{416}$ (x, y) of the biological tissue T with respect to the illumination light IL that transmitted through the optical filters 415 and 416 are calculated using the following Expressions 16 and 17 (S5).

$$A_{415}(x,y) = -\log[SR_{415}(x,y)] \quad \text{(EXPRESSION 16)}$$

$$A_{416}(x,y) = -\log[SR_{416}(x,y)] \quad \text{(EXPRESSION 17)}$$

It is noted that the absorbances $A_{415}$ (x, y) and $A_{416}$ (x, y) can be approximately calculated using the following Expressions 18 and 19.

$$A_{415}(x,y) = -SR_{415}(x,y) \quad \text{(EXPRESSION 18)}$$

$$A_{416}(x,y) = -SR_{416}(x,y) \quad \text{(EXPRESSION 19)}$$

Furthermore, the spectral analysis can be executed simply by eliminating the above mentioned standardization processes (S3, S4). In this case, the absorbances $A_{415}$ (x, y) and $A_{416}$ (x, y) are calculated using the following Expressions 20 and 21.

$$A_{415}(x,y) = -\log G_{415}(x,y) \quad \text{(EXPRESSION 20)}$$

$$A_{416}(x,y) = -\log G_{416}(x,y) \quad \text{(EXPRESSION 21)}$$

Also, in this case, the absorbances $A_{415}$ (x, y) and $A_{416}$ (x, y) can be approximately calculated using the following Expressions 22 and 23, respectively.

$$A_{415}(x,y) = -G_{415}(x,y) \quad \text{(EXPRESSION 22)}$$

$$A_{416}(x,y) = -G_{416}(x,y) \quad \text{(EXPRESSION 23)}$$

Furthermore, as is obvious from the relationships between the absorption wavelength ranges R1, R2 and R3 of hemoglobin and the transmission wavelength ranges of the optical filters 415 and 416 shown in FIG. 1, absorbances $A_{R1}$ (x, y), $A_{R2}$ (x, y) and $A_{R3}$ (x, y) of the biological tissue T with respect to the wavelength ranges R1, R2 and R3 and the absorbances $A_{415}$ (x, y) and $A_{416}$ (x, y) of the biological tissue T with respect to the illumination light IL that transmitted through the optical filters 415 and 416 have relationships expressed in the following Expressions 24 and 25.

$$A_{R1}(x,y) + A_{R3}(x,y) = A_{415}(x,y) - kA_{416}(x,y) \quad \text{(EXPRESSION 24)}$$

$$A_{R2}(x,y) = kA_{416}(x,y) \quad \text{(EXPRESSION 25)}$$

Therefore, the index X (Expression 10) is expressed by the following Expression 26.

(EXPRESSION 26)
$$\begin{aligned} X(x, y) &= [A_{R1}(x, y) + A_{R3}(x, y)] - A_{R2}(x, y) \\ &= [A_{415}(x, y) - kA_{416}(x, y)] - kA_{416}(x, y) \\ &= A_{415}(x, y) - 2kA_{416}(x, y) \end{aligned}$$

Here, k is a constant (correction coefficient). Since the width of the transmission wavelength ranges of the optical filters 415 and 416 differ significantly, the light amounts that transmit through the two filters also differ significantly. Therefore, as mentioned above, the dimmer filter 419 is provided over the optical filter 415, which has a large transmitting light amount, to control the light amount so that a proper exposure can be obtained with the same exposure time even if the optical filter is switched. As a result, a quantitative relationship between the absorbance $A_{415}$ (x, y) acquired using the optical filter 415 and the absorbance $A_{416}$ (x, y) acquired using the optical filter 416 is broken. Also, the transmittances of the optical filters 415 and 416 within the transmission wavelength ranges are not 100% and the optical filters 415 and 416 have transmission losses that vary depending thereon. Furthermore, there are errors in the transmission wavelength ranges of the optical filters 415 and 416. Therefore, even if the dimmer filter 419 is not used, the quantitative relationship between the absorbance $A_{415}$ (x, y) and the absorbance $A_{416}$ (x, y) includes a constant error. The correction coefficient k is a constant for correcting the error of the quantitative relationship between the absorbance $A_{415}$ (x, y) and the absorbance $A_{416}$ (x, y). A method for acquiring the correction coefficient k will be described later. It is noted that, in case this correction is not executed, the correction coefficient k is set at 1.

Further, the following Expression 27 can be obtained by arranging Expression 26 using Expressions 16 and 17.

(EXPRESSION 27)

$$\begin{aligned} X &= -\log[SR_{415}(x, y)] + 2k\log[SR_{416}(x, y)] \\ &= -\log\left[\frac{G_{415}(x, y)/BL_{415}(x, y)}{R_{417}(x, y)/BL_{417}(x, y)}\right] + 2k\log\left[\frac{G_{416}(x, y)/BL_{416}(x, y)}{R_{417}(x, y)/BL_{417}(x, y)}\right] \\ &= -\{[\log G_{415}(x, y) - \log BL_{415}(x, y)] - \\ &\quad [\log R_{417}(x, y) - \log BL_{417}(x, y)]\} + \\ &\quad 2k\{[\log G_{416}(x, y) - \log BL_{416}(x, y)] - \\ &\quad [\log R_{417}(x, y) - \log BL_{417}(x, y)]\} \\ &= -[\log G_{415}(x, y) - \log BL_{415}(x, y)] + \\ &\quad 2k[\log G_{416}(x, y) - \log BL_{416}(x, y)] + \\ &\quad (1 - 2k)[\log R_{417}(x, y) - \log BL_{417}(x, y)] \end{aligned}$$

Therefore, the value of index X can be calculated from the G digital image data $G_{415}$ (x, y) and $G_{416}$ (x, y), R digital image data $R_{417}$ (x, y), and the baseline image data $BL_{415}$ (x, y), $BL_{416}$ (x, y) and $BL_{417}$ (x, y) by using Expression 27 (S6).

Further, the index X can also be approximately calculated using the following Expression 28.

$$X = -\log[SR_{415}(x,y)] + 2k\log[SR_{416}(x,y)] \approx -SR_{415}(x,y) + 2kSR_{416}(x,y) \quad \text{(EXPRESSION 28)}$$

A value list indicating the quantitative relationship between the oxygen saturation and the index X experimentally acquired in advance is stored in a non-volatile memory 532 provided to the controller 530. The controller 530 refers to this value list to acquire an oxygen saturation $SatO_2$ (x, y) which corresponds to a value of the index X calculated using Expression 27 or 28. Then, the controller 530 generates image data (oxygen saturation distribution image data) of which pixel value of each pixel (x, y) is a value obtained by multiplying the acquired oxygen saturation $SatO_2$ (x, y) by a predetermined value (S7).

Figure 7:
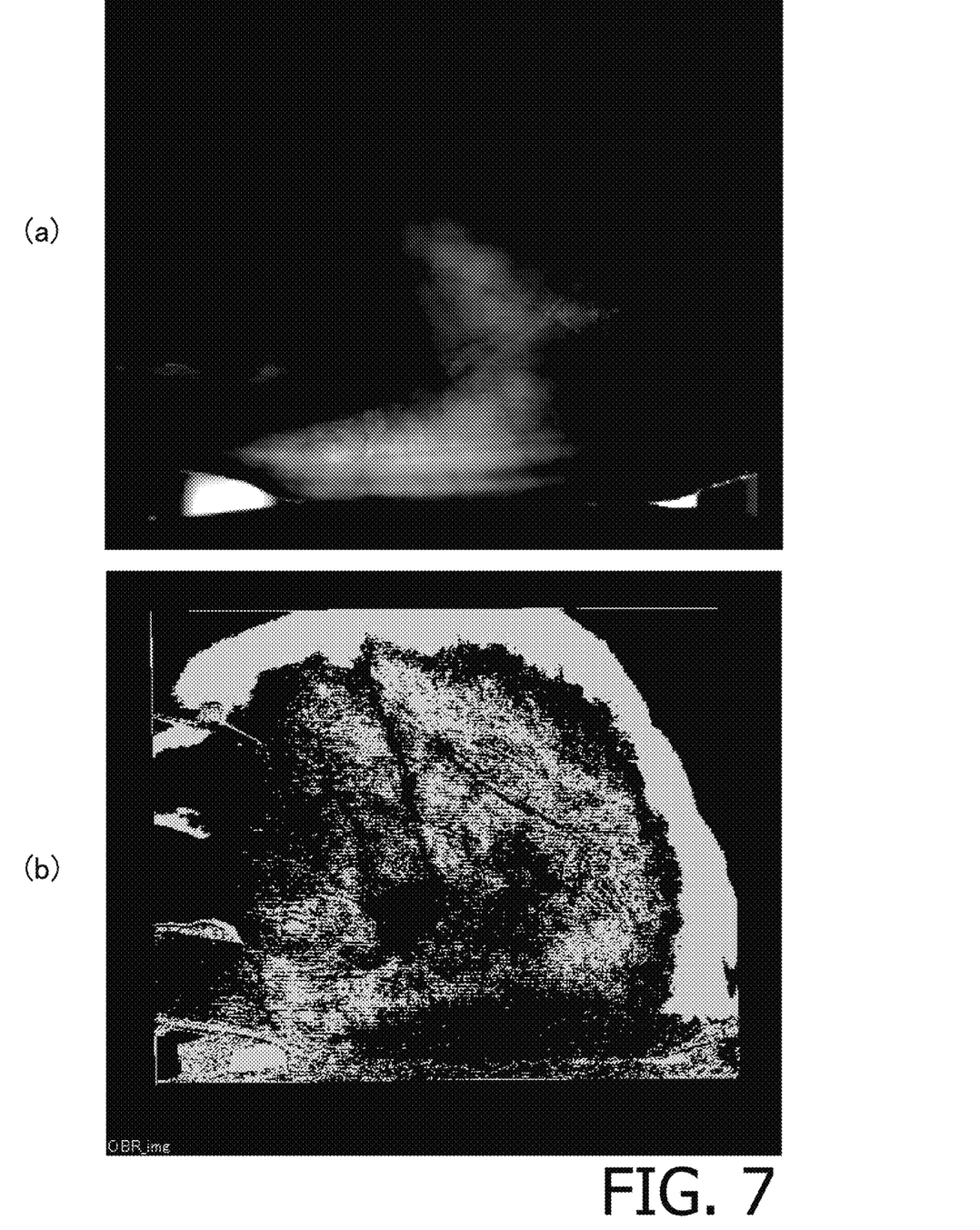
FIG. 7 shows exemplary endoscopic images generated using an endoscope device according to the embodiment of the present invention. (a) is a normal observation image, and (b) is an oxygen saturation distribution image.

Also, the controller 530 generates normal observation image data from the R digital image data $R_{418}$ (x, y), G digital image data $G_{418}$ (x, y) and B digital image data $B_{418}$ (x, y) acquired using the illumination light IL (white light) that transmitted through the optical filter (ultraviolet cut filter) 418. FIG. 7 shows display examples of image data generated by the controller 530. FIG. 7 (a) is an exemplary displayed image of the normal observation image data, and FIG. 7 (b) is an exemplary display image of the oxygen saturation distribution image data.

Further, the controller 530 generates screen image data for arranging and displaying the normal observation image and the oxygen saturation distribution image on a single screen from the generated oxygen saturation distribution image data and normal observation image data, and stores the screen data in the video memory 540. It is noted that the controller 530 can generate a variety of screen images such as a screen image that only displays the oxygen saturation distribution image, a screen image that only displays the normal observation image, or a screen image on which associated information such as patient's ID information or observation condition is superimposed on the oxygen saturation distribution image and/or the normal observation image in accordance with the user's operations.

Next, a method for determining the correction coefficient k in the calibration mode will be described. In the present embodiment, a theoretically calculated index X and a measured index X are compared, and the correction coefficient k is determined such that the measured index X becomes closest to the theoretically calculated index X.

Figure 6:
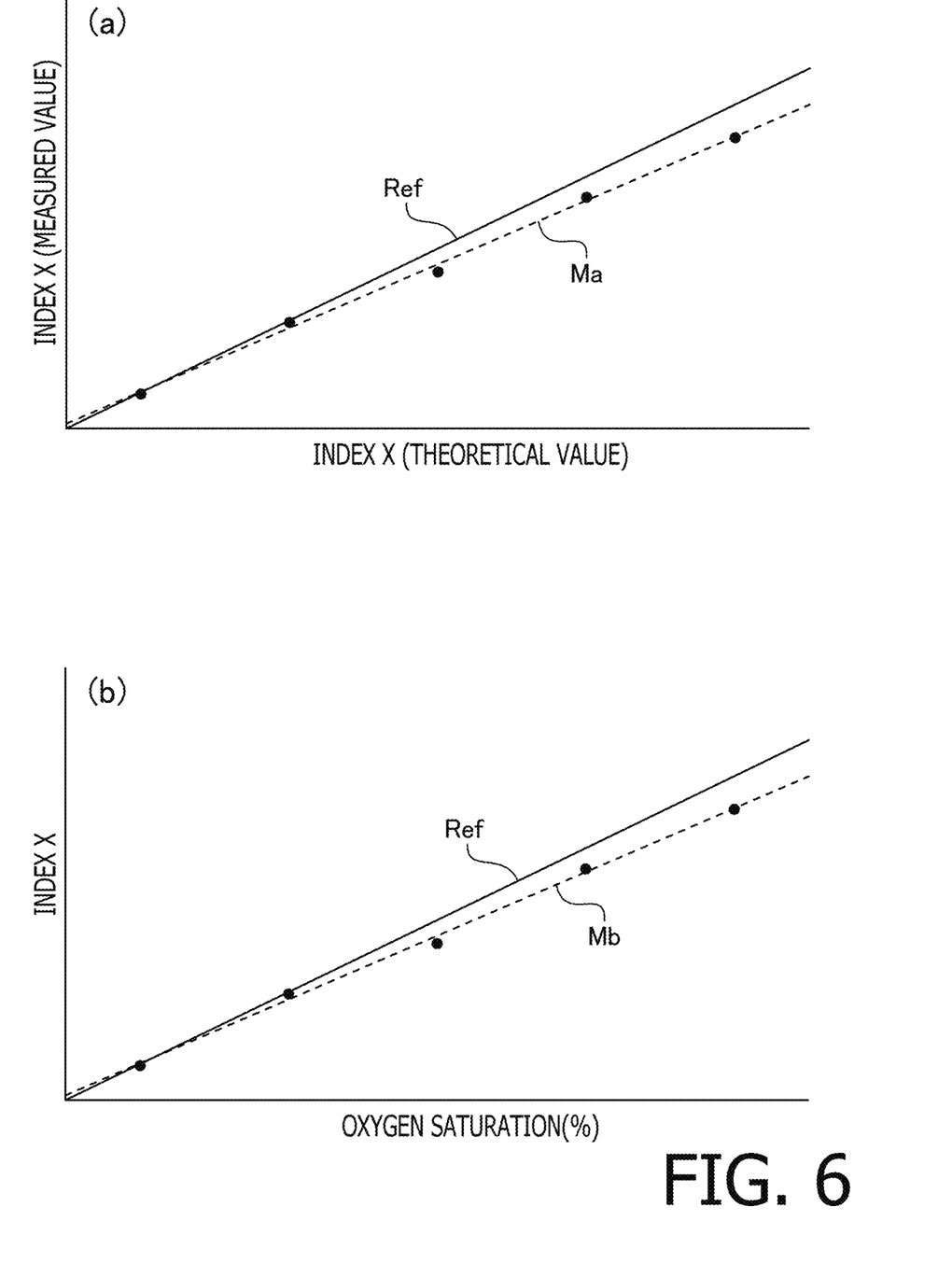
FIG. 6 shows exemplary calibration curves used to determine a correction coefficient k.

FIG. 6 shows exemplary calibration curves used to determine the correction coefficient k in the embodiment of the present invention. FIG. 6 (a) is an example of a common calibration curve of which the horizontal axis is the theoretical index X and the vertical axis is the measured index X acquired by the above explained analyzing process. The filled circles are plots of the measured values, and the broken line Ma is a straight line fitted to the measured value by a least-square method. Further, the solid line shows a reference line Ref representing plots in case measured values equivalent to the theoretical values are obtained.

The measured index X is acquired by the analyzing process using a sample of a biological tissue of which the oxygen saturation is known (e.g., blood). Further, the theoretical index X defined by Expression 26 is calculated using transmission spectra of the optical filters 415 and 416 to be actually used and a reflection spectrum (or absorption spectrum) of blood. Specifically, the theoretical index X is calculated using Expression 26 by using a value obtained by multiplying the transmission spectrum of the optical filter 415 (optical filter 416) by the reflection spectrum of blood and integrating the product as the absorbance $A_{415}$ (absorbance $A_{416}$).

A discrepancy between the Reference line Ref and the measured value Ma is expressed as a gradient of the calibration curve. A phenomenon of which sufficient sensitivity cannot be obtained, that is, a phenomenon of which the gradient is small, is due to an inappropriate quantitative relationship between the absorbance $A_{415}$ (x, y) and the absorbance $A_{416}$ (x, y) in Expression 26, caused by the use of the dimmer filter 419. By selecting an appropriate value as the correction coefficient k, an error caused by the dimmer filter 419 can be corrected, and thus a state in which an error between the measured index X and the theoretical index X is minimized and the measured index X has the highest correlational relationship with the theoretical index X can be achieved.

FIG. 6 (b) is a variation of the calibration curve. In the calibration curve shown in FIG. 6 (b), the horizontal axis is the oxygen saturation of a sample, and the vertical axis is the index X. The filled circles are plots of the measured values, and the broken line Ma is a straight line fitted to the measured value by a least-square method. Further, the solid line Mb shows the theoretically calculated values. It is noted that the oxygen saturations of the sample are correctly measured values acquired from an ideal spectrometry. Being a curve obtained by changing the horizontal scale of the calibration curve shown in FIG. 6 (a), this calibration curve is substantially equivalent to the curve of FIG. 6 (a), but there is an advantage that a correct relationship with the oxygen saturation can be easily read.

It is noted that, although the above-explained method for determining the correction coefficient k using the calibration curve is a method in which analysis results of a plurality of samples having different oxygen saturations are used, the correction coefficient k can also be determined using an analysis result from only one sample.

Also, focusing on the absorption wavelength ranges R1, R2 and R3 of hemoglobin (i.e., the transmission wavelength of the optical filter 415), the absorbances $A_{R1}(x, y)$, $A_{R2}(x, y)$ and $A_{R3}(x, y)$ change in accordance with the change in the oxygen saturation, but a sum Y of these absorbances (shown in Expression 29) is substantially constant. Furthermore, since the sum Y of the absorbances is in proportion to a total amount of hemoglobin (a sum of oxyhemoglobin $HbO_2$ and deoxyhemoglobin Hb) in a biological tissue, it is reasonable to use the sum Y as an index for the total amount of hemoglobin.

$$Y(x,y)=A_{R1}(x,y)+A_{R2}(x,y)+A_{R3}(x,y)=A_{415} \quad \text{(EXPRESSION 29)}$$

It is known that, in a tissue of a malignant tumor, the total amount of hemoglobin is greater than that of a healthy tissue due to angiogenesis and the oxygen saturation is lower than that of a healthy tissue due to notable oxygen metabolism. Therefore, the controller 530 can extract pixels of which the index Y, calculated using Expression 29 and indicating the total amount of hemoglobin, is greater than a predetermined reference value (first reference value) and the index X, calculated using Expression 25 and indicating the oxygen saturation, is smaller than a predetermined reference value (second reference value); generate, for example, lesion region highlighting image data in which highlighting process is executed to pixels corresponding to the extracted pixels in the normal observation image data; and display the lesion region highlighting image along with the normal observation image and/or the oxygen saturation distribution image (or alone) on the monitor 300.

Exemplary highlighting process includes a process for increasing pixel values of corresponding pixels, a process for changing color phases (for example, a process for increasing the R component to change to a reddish color or a process for rotating the color phase for a predetermined angle), and a process for making the corresponding pixels blink (or periodically changing the color phase).

Further, for example, the controller 530 may be configured to calculate an index Z (x, y) indicating a probability of being a malignant tumor on the basis of a deviation from an average of the index X (x, y) and a deviation from an average of the index Y (x, y), and to generate image data with the index Z (x, y) as pixel values (malign probability image data) instead of the lesion region highlighting image data.

The above is an explanation of an embodiment of the present invention and specific examples of the embodiment. However, the present invention is not limited to the above configuration and various modifications are possible within the technical ideas of the present invention.

In the above embodiment, the pixel value of the oxygen saturation distribution image is calculated by acquiring an oxygen saturation value from the value list in accordance with a value of the index X and by multiplying the oxygen saturation by a predetermined constant, but the present invention is not limited to this configuration. Since the index X is a value that monotonically increases with the oxygen saturation, the index X itself (or the index X multiplied by a predetermined constant) may be used as a pixel value of the oxygen saturation distribution image.

Further, the image pick-up device 141 of the present embodiment is explained as an image pick-up device for taking color images comprising primary color filters R, G, B on its front face, but the image pick-up device is not limited to this configuration. For example, an image pick-up device for taking color images comprising complementary color filters Y, Cy, Mg, G may be used.

Further, the image pick-up device 141 of the present embodiment is explained as a pick-up device for taking color images comprising an on-chip color filter 141a, but the image pick-up device is not limited to this configuration. For example, an image pick-up device for taking black-and-white images may be used to configure an image pick-up device comprising a so-called frame sequential type color filter. Also, the color filter 141a is not limited to an on-chip configuration but may be positioned on a light path between the light source 430 and the image pick-up device 141.

Further, in the above embodiment, the rotating filter 410 is used, but the present invention is not limited to this configuration. Other types of wavelength variable filter of which transmission wavelength can be switched may also be used.

Further, in the above embodiment, a configuration in which the rotating filter 410 is provided at the light source side and the illumination light IL is filtered, but the present invention is not limited to this configuration. The rotating filter 410 may be provided at the image pick-up device side (for example, between the objective optical system 121 and the image pick-up device 141) and configured to filter a return light from an object.

Further, in the above embodiment, a configuration in which the rotating filter 410 is rotated at constant rotation speed while taking images at predetermined time intervals in the spectral analysis mode is adopted, but the present invention is not limited to this configuration. For example, a device may be configured such that the rotating position of the rotating filter 410 changes step by step at predetermined time intervals and images are taken while the rotation of the rotating filter is stopped.

Further, the above embodiment is an example in which the present invention is applied to an electronic endoscope device being a form of a digital camera, but the present invention can also be applied to systems that use other types of digital camera (e.g., digital single lens reflex camera or digital video camera). For example, if the present invention is applied to a digital still camera, observation of surface tissue or observation of brain tissue during craniotomy (e.g., a quick inspection of cerebral blood flow) can be performed.

DESCRIPTION OF SYMBOLS 1 spectral endoscope device
100 electronic endoscope
110 insertion tube 111 insertion tube tip portion
121 objective optical system
131 light guide
131a tip portion
131b end portion
132 lens
141 image pick-up device
141a color filter
142 cable
200 processor for electronic endoscope
300 monitor
400 light source unit
410 rotating filter
420 filter control unit
430 light source
440 collimator lens
450 condenser lens
500 image processor unit
510 A/D conversion circuit
520 temporary memory
530 controller
540 video memory
550 signal processing circuit

What is claimed is:

1. A device that generates a distribution image showing a molar concentration ratio between a first biological substance and a second biological substance included in a biological tissue of which an absorption spectrum within a predetermined wavelength range has a first isosbestic point, a second isosbestic point, a third isosbestic point and a fourth isosbestic point, wherein the wavelengths of the first, second, third and fourth isosbestic points are about 528 nm, about 546 nm, about 570 nm, and about 584 nm respectively, the device comprising:

a light source which emits white light;
a first optical filter configured to selectively transmit, from the white light, light within a wavelength range from the first isosbestic point to the fourth isosbestic point, and not to transmit light outside the wavelength range, the wavelength range including a first wavelength range from the first isosbestic point to the second isosbestic point, a second wavelength range from the second isosbestic point to the third isosbestic point, and a third wavelength range from the third isosbestic point to the fourth isosbestic point;
a second optical filter configured to selectively transmit light within the second wavelength range from the white light, and not to transmit light outside the second wavelength range;
a controller configured to sequentially insert the first optical filter and the second optical filter one after another, into a light path of the white light emitted by the light source;
an image pick-up device configured to take a first image of the biological tissue using the light transmitted through the first optical filter and a second image of the biological tissue using the light transmitted through the second optical filter; and
an image processor configured to generate the distribution image on the basis of the first image and the second image;
wherein the first and second biological substances are oxyhemoglobin and deoxyhemoglobin,
wherein the molar concentration ratio of the first biological substance and the second biological substance included in the biological tissue is oxygen saturation,
wherein the first optical filter has a transmission wavelength range of about 528 nm-584 nm and the second optical filter has a transmission wavelength range of about 546 nm-570 nm, and
wherein the image processor generates the distribution image on the basis of the first image and the second image by acquiring a first absorbance of the biological tissue in a transmission wavelength range of the first optical filter on the basis of the first image, acquiring a second absorbance of the biological tissue in a transmission wavelength range of the second optical filter on the basis of the second image, and calculating an index X, as $X=A_1-2kA_2$ where k is a constant, $A_1$ is the first absorbance, $A_2$ is the second absorbance; and generating the distribution image on the basis of the index X.

2. The device according to claim 1 comprising an endoscope device including an endoscope provided with the image pick-up device at a tip portion of the endoscope.

3. The device according to claim 1,
wherein the predetermined wavelength range is a Q band of hemoglobin, and
wherein the first image and the second image are images taken by a light-receiving element, to which a G filter is provided, included in the device provided with an RGB color filter.

* * * * *